United States Patent [19]

Reiner et al.

[11] Patent Number: 5,093,361
[45] Date of Patent: Mar. 3, 1992

[54] D-2-(6-METHOXY-2-NAPHTHYL)-PROPIONIC ACID AND PHARMACEUTICAL COMPOSITIONS CONTAINING IT

[75] Inventors: Valentina Reiner, Carate Urio; Caterina Sarda, Como, both of Italy

[73] Assignee: Farma Resa S.r.l., Cantu, Italy

[21] Appl. No.: 485,084

[22] Filed: Feb. 26, 1990

[30] Foreign Application Priority Data

Jan. 29, 1990 [IT] Italy ................ 19184 A/90

[51] Int. Cl.⁵ .................... A61K 31/21; C07C 327/00
[52] U.S. Cl. ................. 514/513; 558/254
[58] Field of Search ............ 558/254; 514/513

[56] References Cited
FOREIGN PATENT DOCUMENTS 0124925 11/1986 European Pat. Off. ............ 558/254

Primary Examiner—David B. Springer
Assistant Examiner—Robert C. Whittenbaugh
Attorney, Agent, or Firm—Wenderoth, Lind & Ponack

[57] ABSTRACT

The S-[d-2-(6-methoxy-2-naphthyl)-propionyl]d-2-mercaptopropionamidoacetic acid having formula:

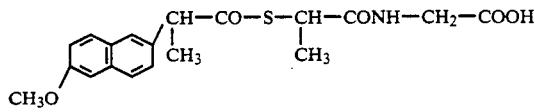

has improved therapeutic properties not only in comparison with the starting active principle, namely Naproxen, but also with respect to the corresponding racemic derivative, namely the (d,l) compound.

2 Claims, No Drawings

D-2-(6-METHOXY-2-NAPHTHYL)-PROPIONIC ACID AND PHARMACEUTICAL COMPOSITIONS CONTAINING IT

The present invention relates to an optically active isomer of a derivative of d-2-(6-methoxy-2-naphthyl)-propionic acid, namely of the active principle known as Naproxen; the invention relates as well to pharmaceutical compositions containing the said derivative.

Naproxen is known since a number of years and is included among the substances having anti-inflammatory, analgesic and anti-pyretic activity. Its main therapeutic use is the treatment of rheumatoid arthritis and of other degenerative forms having phlogistic features.

In turn, alpha-mercaptopropionylglycine is a compound known as well, possessing also anti-inflammatory activity besides the mucolytic activity.

The derivatives obtained by combining the said two active principles are the object of the European Patent No. 124.925, which thus claims compounds having the following general formula:

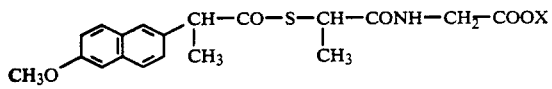

wherein X is hydrogen or a radical selected from among organic radicals or inorganic radicals, non toxic and pharmaceutically acceptable bases, radicals of basic aminoacids and radicals of basic antibiotics.

The characteristics and properties of the above mentioned compounds in the racemic form, namely the (d,l) form, are given in the specification and in the examples of this European Patent.

It has been now found and is the object of the present invention that the (d,d) diastereoisomer of the compound directly obtained from Naproxen and alpha-mercaptopropionylglycine has surprisingly specific properties which are superior not only to respect with the starting active principle, namely Naproxen, but also with respect to the corresponding (d,l) racemic compound.

This greater activity over Naproxen is mainly seen in the lack of ulcerogenicity which is on the contrary the main drawback of Naproxen as regards the therapeutical use; whereas in comparison with the corresponding racemic compound, the diastereoisomer of the present invention has greater analgesic activity.

Otherwise stated, the diastereoisomer of the present invention to the prevailing anti-inflammatory activity which is characteristic both of Naproxen and more remarkably of the derivatives being the subject of the European Patent 124.925, adds a specific analgesic activity which is definitely higher than that the of the corresponding racemic compound.

It is evident that the therapeutical use of these substances makes the symptomatic activity, namely the analgesic one, of the utmost importance.

As regards the preparation of the diastereoisomer of the present invention, reference is made to the specification and examples of European Patent 124.925, particularly examples 1a and 1b of this patent, which is herein included by reference.

Thus according to the process studied with respect to the present invention, the product of the reaction carried out between the acid chloride of d-2-(6-methoxy-2-naphthyl)-propionic acid and (2-mercapto-propionyl)-glycine in the presence of a base is poured in water, then an acidification is carried out with hydrochloric acid and the solid thus precipitated is filtered. For the separation of the desired (d,d) form; repeated fractionated crystallizations, of the racemic one are carried out, using ethyl acetate as the crystallization solvent, until a product having constant melting point (180-1° C.) is obtained.

The obtained compound has been subjected to elemental analysis with the following results:
Calculated for $C_{19}H_{21}NO_5S$: %C 60.78; %H 5,63; %N 3,73; %S 8,54
Found: %C 61.02; %H 5.59; %N3,71; %S 8.63.

The (d,d) diastereoisomer of the invention is a crystalline solid having $[alpha]_D^{20} + 201.01$ (C=1, methanol).

It is soluble in ethanol, methanol and acetone, a little soluble in hot ethyl acetate and insoluble in water.

By carrying out the TLC analysis with chloroform: glacial acetic acid: water (85:15:0.5) as the eluant system, a value $R_f = 0.75$ is obtained whereas the (d,l) diastereoisomer has $R_f = 0.70$.

The already mentioned properties of the diastereoisomer according to the invention have been confirmed by the pharmacological tests which are hereinafter shortly reported (the compound of the invention is indicated in abbreviated form has d-d Nxtio whereas the other diastereoisomer is abbreviated as d-l Nxtio).

As regards the anti-inflammatory activity, the standard tests by means of carrageenan induced oedema and dextran induced oedema were performed whereas for the analgesic activity the writhing test and the Randall-Selitto test have been carried out.

1. Carrageenan induced oedema in the rat

Groups of 8 rats (Wistar-Charles River) have been orally administered with:
(i) vehicle alone (0.5% tragacanth);
(ii) d-d Nxtio at a constant volume of 24 ml/kg in the same vehicle;
(iii) d-l Nxtio at constant volume of 25 ml/kg in the same vehicle. The table 1 hereinafter reports the administration dosages.

TABLE 1

| GROUP | TREATMENT VEHICLE | DOSE mg/kg p.o. |
|---|---|---|
| 1 | vehicle | — |
| 2 | | 6.25 |
| 3 | | 12.5 |
| 4 | d-d Nxtio | 25.0 |
| 5 | | 50.0 |
| 6 | | 6.25 |
| 7 | | 12.5 |
| 8 | d-l Nxtio | 25.0 |
| 9 | | 50.0 |

Forty five minutes later each rat received an injection of 0.1 ml of a 1% w/v suspension of carrageenan in sterile 0.9% saline, beneath the plantar aponeurosis of the left hind paw.

The volume of the paw was measured (in arbitrary units) before and 1.5, 3 and 6 hours after the irritant injection. The results are reported in the table 2, from which it can be observed not only that both diastereoisomers administered by oral route induce a significant inhibition of the carrageenan induced oedema, but also that d-l isomer is slightly less active than the d-d isomer.

TABLE 2

| | | DOSE mg/Kg | MEAN INCREASE IN PAW VOLUME | | | % INHIBITION OF SWELLING | | |
|---|---|---|---|---|---|---|---|---|
| GROUP | TREATMENT | p.o. | 1.5 | 3 | 6 | 1.5 | 3 | 6 |
| 1 | vehicle | | 7.9 ± 0.58 | 12.1 ± 0.52 | 13.4 ± 0.76 | — | — | — |
| 2 | d-d Nxtio | 6.25 | 3.7 ± 0.59 | 5.5 ± 0.57 | 8.1 ± 0.44 | 53.2 | 54.5 | 39.6 |
| 3 | | 12.5 | 4.7 ± 0.95 | 8.9 ± 0.90 | 8.7 ± 1.12 | 40.5 | 26.4 | 35.1 |
| 4 | | 25.0 | 4.3 ± 0.59 | 8.3 ± 0.95 | 9.8 ± 0.86 | 45.6 | 31.4 | 26.9 |
| 5 | | 50.0 | 5.0 ± 0.94 | 8.4 ± 0.76 | 8.4 ± 0.86 | 36.7 | 30.6 | 37.3 |
| 6 | d-l Nxtio | 6.25 | 4.1 ± 0.61 | 6.2 ± 0.62 | 8.7 ± 0.55 | 48.1 | 48.7 | 35.0 |
| 7 | | 12.5 | 4.9 ± 0.92 | 9.3 ± 1.10 | 9.4 ± 1.12 | 37.9 | 23.1 | 29.8 |
| 8 | | 25.0 | 4.6 ± 0.70 | 8.9 ± 1.2 | 10.2 ± 0.81 | 41.7 | 26.4 | 23.8 |
| 9 | | 50.0 | 5.6 ± 0.92 | 8.7 ± 0.8 | 9.8 ± 0.84 | 29.1 | 28.0 | 26.8 |

Effects of oral administration of d-d Nxtio and d-l Nxtio on a carrageenan-induced oedema in the rat 2. ran induced oedema in the rat This test has been carried out like the preceding one, except that instead of carrageenan 0.1 ml of a 6% suspension w/v of dextran in the same sterile saline solution where injected.

The measurement of the paw volume (in milliliters) was carried out before the injection and at 0.5, 1 and 2.5 hours after the injection.

The results reported in the table 3 confirm the anti-inflammatory activity of both isomers, with a slight superiority of d-d isomer.

TABLE 3

Effects of oral administration of d-d Nxtio and d-l Nxtio on a dextran-induced oedema in the rat

| | | DOSE mg/Kg | MEAN INCREASE IN PAW VOLUME | | | % INHIBITION OF SWELLING | | |
|---|---|---|---|---|---|---|---|---|
| GROUP | TREATMENT | p.o. | 0.5 | 1 | 2.5 | 0.5 | 1 | 2.5 |
| 1 | vehicle | | 1.09 ± 0.05 | 1.28 ± 0.04 | 1.08 ± 0.06 | — | — | — |
| 2 | d-d Nxtio | 6.25 | 1.03 ± 0.04 | 1.00 ± 0.03 | 0.72 ± 0.04 | 5.5 | 21.9 | 33.3 |
| 3 | | 12.5 | 1.12 ± 0.06 | 1.16 ± 0.04 | 0.83 ± 0.06 | 0 | 9.4 | 23.2 |
| 4 | | 25.0 | 1.09 ± 0.02 | 1.11 ± 0.04 | 0.81 ± 0.03 | 0 | 13.3 | 25.0 |
| 5 | | 50.0 | 1.24 ± 0.05 | 0.90 ± 0.04 | 0.73 ± 0.02 | 0 | 29.7 | 32.4 |
| 6 | d-l Nxtio | 6.25 | 1.04 ± 0.08 | 1.03 ± 0.07 | 0.85 ± 0.07 | 4.6 | 19.5 | 21.3 |
| 7 | | 12.5 | 1.11 ± 0.04 | 1.11 ± 0.08 | 0.79 ± 0.08 | 0 | 13.3 | 26.8 |
| 8 | | 25.0 | 1.12 ± 0.06 | 1.14 ± 0.06 | 0.80 ± 0.06 | 0 | 11.0 | 26.0 |
| 9 | | 50.0 | 1.20 ± 0.05 | 1.10 ± 0.04 | 0.9 ± 0.04 | 0 | 14.0 | 16.6 |

3. Writhing test in the rat

Groups of 10 rats (Wistar-Charles River) were dosed orally with either vehicle (0.5% tragacanth) or test compounds (d-d and d-1 Nxtio) at a costant volume of 10 ml/kg according to the treatment table 1.

Forty-five minutes later each rat received an intraperitoneal injection of 1.0 ml of 1% solution of acetic acid. They were then placed in individual cages and the number of writhes elicited by each rat in the following 25 minute period was recorded.

The results of this test are reported in the table 4, from which it can be observed that both diastereoisomers cause a dose dependent inhibition, with a marked superiority of the isomer d-d of the order of 20%.

TABLE 4

Analgesic activities of orally administered compounds in the writhing test - individual animal data

| TREATMENT | ORAL DOSE (mg/Kg) | NUMBER OF WRITHES/25 MIN FOR ANIMAL No. | | | | | | | | | | MEAN WRITHING SCORE (± s.e.) |
|---|---|---|---|---|---|---|---|---|---|---|---|---|
| | | 1 | 2 | 3 | 4 | 5 | 6 | 7 | 8 | 9 | 10 | |
| Vehicle | — | 49 | 54 | 40 | 65 | 43 | 48 | 23 | 65 | 19 | 57 | 46.3 ± 5.24 |
| d-d Nxtio | 50 | 4 | 10 | 16 | 4 | 24 | 4 | 8 | 6 | 3 | 1 | 8.0 ± 2.36 |
| | 25 | 35 | 7 | 16 | 16 | 5 | 36 | 16 | 36 | 23 | 21 | 21.1 ± 3.81 |
| | 12.5 | 42 | 61 | 23 | 25 | 39 | 48 | 38 | 43 | 9 | 7 | 33.5 ± 5.74 |
| | 6.25 | 47 | 59 | 33 | 46 | 71 | 23 | 26 | 25 | 24 | 47 | 40.1 ± 5.52 |
| d-l Nxtio | 50 | 7 | 12 | 10 | 8 | 24 | 7 | 11 | 5 | 9 | 0 | 9.3 ± 1.95 |
| | 25 | 24 | 15 | 32 | 15 | 7 | 28 | 25 | 31 | 20 | 25 | 22.2 ± 2.51 |
| | 12.5 | 56 | 65 | 31 | 37 | 44 | 52 | 35 | 41 | 25 | 10 | 39.6 ± 5.03 |
| | 6.25 | 48 | 51 | 45 | 39 | 31 | 34 | 46 | 37 | 26 | 72 | 42.9 ± 4.09 |

4. Randall-Selitto test in the rat

Male Wistar rats (70-90 g) were starved 18 hours prior to the commencement of the experiment but water was available ad libitum.

Each rat received an injection of 0.1 ml of a 20% suspension of Brewer's yeast in distilled water beneath the plantar aponeurosis of the left hind paw.

One hour later the pain thresholds of both the inflamed (yeast injected) and normal hind paw were measured using an analgesiometer designed by U. Basile; the animals were then dosed orally with vehicle (0.5% tragacanth) or test compounds at a constant dose volume of 10 ml/kg.

There were 10 rats in each drug-treated group and 20 rats in the vehicle-treated group.

The pain thresholds of the inflamed and normal hind paws were again measured at 1, 2 and 4 hours after dosing.

The results are reported in the table 5 from which it can be observed not only a peak of analgesic effect at two hours from the administration but also the superiority of the (d-d) isomer.

In this connection reference is made to the disclosure of European Patent 124.925, which is here incorporated for reference.

The dosages of active principles shall be still those of the corresponding composition based on Naproxen whereby the therapeutical effect is obviously increased.

TABLE 5

Changes in pain threshold of inflamed and normal paws of rats receiving oral treatment with d-d Nxtio and d-l Nxtio

| | | | MEAN CHANGE IN PAIN THRESHOLD (G ± S.E.) FROM PRE-DOSE AT POST-DOSE TIME | | | | | |
|---|---|---|---|---|---|---|---|---|
| | | DOSE | 1 HOUR | | 2 HOURS | | 4 HOURS | |
| GROUP | TREAT-MENT | (mg/Kg) p.o. | INFLAMED PAW | NORMAL PAW | INFLAMED PAW | NORMAL PAW | INFLAMED PAW | NORMAL PAW |
| 1 | vehicle | — | −22.4 ± 15.2 | −40.5 ± 17.8 | −42.0 ± 15.1 | −52.6 ± 18.0 | −21.3 ± 15.3 | −39.2 ± 13.9 |
| 2 | d-d Nxtio | 6.25 | −27.2 ± 30.8 | −12.8 ± 17.8 | −42.2 ± 21.9 | −17.7 ± 18.2 | −32.7 ± 15.5 | 34.1 ± 17.4 |
| 3 | | 12.5 | 32.6 ± 40.1 | −13.7 ± 22.9 | 32.6 ± 41.7 | −23.4 ± 18.2 | 38.9 ± 48.6 | 10.7 ± 23.7 |
| 4 | | 25 | 53.2 ± 29.9 | −1.0 ± 26.0 | 31.3 ± 35.8 | −33.5 ± 24.4 | 41.9 ± 35.3 | 18.7 ± 35.9 |
| 5 | | 50 | 48.3 ± 27.9 | −1.3 ± 22.9 | 98.9 ± 38.9 | −38.8 ± 18.9 | 79.4 ± 42.7 | 25.7 ± 24.3 |
| 6 | d-l Nxtio | 6.25 | −21.6 ± 30.9 | −14.3 ± 20.0 | −38.4 ± 18.9 | −24.5 ± 25.3 | −23.1 ± 18.4 | −10 ± 25.5 |
| 7 | | 12.5 | 25.5 ± 37.3 | −15.4 ± 29.6 | 20.5 ± 38.7 | −20.9 ± 25.6 | 21.2 ± 43.2 | −12 ± 15.8 |
| 8 | | 25 | 40.2 ± 31.4 | −10.8 ± 27.5 | 23.2 ± 34.6 | −31.5 ± 21.9 | 29.6 ± 38.1 | 19 ± 37.7 |
| 9 | | 50 | 42.3 ± 31.6 | −1.4 ± 10.3 | 60.2 ± 45.7 | −38.4 ± 22.8 | 52.1 ± 19.1 | 18 ± 22.7 |

At this point it is worth to noting that the advantages achieved by the present invention must be evaluated as a function of the relevant advancement already achieved with the compounds of the European Patent 124.925 whereby the further improvement which is thus obtained is, in obviously relative terms, a result relevant as well and fully unforeseable.

The pharmaceutical compositions according to the present invention comprise as the active ingredient the (d-d) diastereoisomer together with the standard vehicles and excipients.

We claim:

1. A method for achieving anti-inflammatory and analgesic effect in a patient in need of such treatment which comprises administering to such patient an effective amount of S-d-2-mercaptopropionamido acetic acid.

2. A pharmaceutical composition useful in achieving anti-inflammatory and analgesic effect in a patient and suitable for administration by oral, topical or rectal route which comprises an effective amount of S-d-2-mercaptopropionamido acetic acid and a pharmaceutically acceptable carrier therefor.

* * * * *